US010921021B2

United States Patent
Schmider et al.

(10) Patent No.: US 10,921,021 B2
(45) Date of Patent: Feb. 16, 2021

(54) MODULAR BLOOD WARMER

(71) Applicant: WWT Technischer Geraetebau GmbH, Stuttgart (DE)

(72) Inventors: Klaus Schmider, Stuttgart (DE); Axel Stihler, Stuttgart (DE); Wolfgang Theilacker-Beck, Stuttgart (DE); Matthias Theilacker, Stuttgart (DE)

(73) Assignee: WWT Technischer Geraetebau GmbH, Stuttgart (DE)

( * ) Notice: Subject to any disclaimer, the term of this patent is extended or adjusted under 35 U.S.C. 154(b) by 554 days.

(21) Appl. No.: 15/465,628

(22) Filed: Mar. 22, 2017

(65) Prior Publication Data

US 2017/0276402 A1    Sep. 28, 2017

(30) Foreign Application Priority Data

Mar. 23, 2016  (DE) .................... 10 2016 204 778.7
Jun. 3, 2016   (DE) .................... 10 2016 209 769.5
Jul. 22, 2016  (DE) .................... 10 2016 213 422.1

(51) Int. Cl.
*F24H 1/12*  (2006.01)
*A61M 5/44* (2006.01)
*A61M 1/16* (2006.01)

(52) U.S. Cl.
CPC ........... *F24H 1/121* (2013.01); *A61M 1/1629* (2014.02); *A61M 5/44* (2013.01); *A61M 5/445* (2013.01); *A61M 2205/3368* (2013.01); *A61M 2205/366* (2013.01)

(58) Field of Classification Search
None
See application file for complete search history.

(56) References Cited

U.S. PATENT DOCUMENTS 1,363,947 A  *  12/1920  Youngblood ........... F24H 1/106
                                              392/314
3,074,401 A  *   1/1963  Friedman ................ A61M 1/32
                                               422/46
3,291,568 A  *  12/1966  Santter .................... A61M 1/32
                                               422/46

(Continued)

FOREIGN PATENT DOCUMENTS

DE          27 50 418         5/1978
DE       10 2014 103 590     11/2014

(Continued)

*Primary Examiner* — Thor S Campbell
(74) *Attorney, Agent, or Firm* — Paul Vincent (57) ABSTRACT

A blood warmer (10) has a first heating plate (12) and a second heating plate (14) as well as an exchangeable conductor (18, 20, 22, 24) for blood, which is arranged between the first heating plate (12) and the second heating plate (14). The blood warmer (10) has an inlet (66) and an outlet (68) for blood to which the conductor (18, 20, 22, 24) is fluidically connected. Due to the roughness of the surface (46) of the conductor (18, 20, 22, 24), an intermediate space (50) remains between the first heating plate (12) and/or the second heating plate (14) and the conductor (18, 20, 22, 24). A medium (52), which has a higher thermal conductivity than air, is at least partially statically arranged in the intermediate space (50). The blood warmer (10) may also have an electromechanical oscillating circuit and/or a vibration motor.

18 Claims, 8 Drawing Sheets

(56) References Cited

U.S. PATENT DOCUMENTS

| | | | | |
|---|---|---|---|---|
| 3,374,066 A * | 3/1968 | Farrant | A61M 5/44 | 422/47 |
| 3,399,536 A * | 9/1968 | Heinz | A61M 5/44 | 62/3.2 |
| 3,485,245 A * | 12/1969 | Terwilliger | A61M 5/44 | 604/114 |
| 3,629,552 A * | 12/1971 | Edging | A61M 5/44 | 392/470 |
| 3,853,479 A * | 12/1974 | Talonn | A61M 5/44 | 422/46 |
| 4,065,264 A * | 12/1977 | Lewin | A61M 1/32 | 422/46 |
| 4,293,762 A * | 10/1981 | Ogawa | A61M 5/44 | 165/46 |
| 4,464,563 A * | 8/1984 | Jewett | A61M 5/44 | 137/341 |
| 4,532,414 A | 7/1985 | Shah | | |
| 4,559,999 A * | 12/1985 | Servas | A61M 5/44 | 165/156 |
| 4,583,583 A * | 4/1986 | Wittel | H01M 8/04007 | 165/46 |
| 4,653,577 A * | 3/1987 | Noda | A61M 1/3627 | 165/103 |
| 4,707,587 A * | 11/1987 | Greenblatt | A61M 5/44 | 165/102 |
| 4,759,749 A * | 7/1988 | Verkaart | A61M 5/44 | 165/156 |
| 4,782,212 A * | 11/1988 | Bakke | A61M 5/44 | 165/170 |
| 4,801,777 A * | 1/1989 | Auerbach | A61M 5/445 | 219/687 |
| 4,808,159 A * | 2/1989 | Wilson | A61M 5/445 | 604/113 |
| 4,847,470 A * | 7/1989 | Bakke | A61M 5/44 | 392/470 |
| 4,960,167 A * | 10/1990 | Stenlund | F28D 7/106 | 123/41.33 |
| 5,013,889 A * | 5/1991 | Bakke | A61M 5/44 | 392/401 |
| 5,245,693 A * | 9/1993 | Ford | A61M 5/44 | 165/169 |
| 5,388,634 A * | 2/1995 | Weinstein | A61M 5/44 | 165/67 |
| 5,458,593 A * | 10/1995 | Macabasco | A61J 1/10 | 128/DIG. 24 |
| 5,724,478 A * | 3/1998 | Thweatt | F24H 1/142 | 219/535 |
| 5,899,077 A * | 5/1999 | Wright | F25B 21/02 | 165/168 |
| 6,175,688 B1 * | 1/2001 | Cassidy | A61M 5/365 | 392/470 |
| 6,330,395 B1 * | 12/2001 | Wu | F24H 1/14 | 392/484 |
| 6,336,003 B1 * | 1/2002 | Mitsunaga | A61M 5/44 | 392/470 |
| 6,464,666 B1 * | 10/2002 | Augustine | A61F 7/0085 | 392/470 |
| 6,782,195 B2 * | 8/2004 | Abras | F24H 1/162 | 392/480 |
| 7,046,922 B1 * | 5/2006 | Sturm | F24H 1/102 | 392/465 |
| 7,316,666 B1 * | 1/2008 | Entenman | A61M 5/44 | 392/465 |
| 7,403,704 B2 * | 7/2008 | Eccleston | A61F 7/12 | 392/466 |
| 7,822,326 B2 * | 10/2010 | Commette | F24H 1/102 | 392/465 |
| 9,314,366 B2 * | 4/2016 | Platt | A61F 7/0085 | |
| 2003/0097882 A1 * | 5/2003 | Schlosser | G01F 1/8404 | 73/861.355 |
| 2009/0012655 A1 | 1/2009 | Kienmann | | |
| 2010/0327492 A1 | 12/2010 | Sansoucy | | |
| 2011/0267590 A1 * | 11/2011 | Rodak | G03F 7/70991 | 355/30 |
| 2012/0049512 A1 * | 3/2012 | Hayes, Jr. | F16L 19/0283 | 285/256 |
| 2014/0072288 A1 | 3/2014 | Newell | | |
| 2014/0154442 A1 * | 6/2014 | Bent | A61J 1/10 | 428/35.2 |
| 2017/0361548 A1 * | 12/2017 | Nishimura | B29C 71/02 | |

FOREIGN PATENT DOCUMENTS

| | | |
|---|---|---|
| DE | 10 2014 013 419 | 3/2016 |
| EP | 0 247 989 | 12/1987 |
| WO | WO 01/26719 | 4/2001 |
| WO | WO 2004/098675 | 11/2004 |
| WO | WO 2014/118487 | 8/2014 |

* cited by examiner

MODULAR BLOOD WARMER

This application claims Paris convention priority from DE 10 2016 204 778.7 filed Mar. 23, 2016, DE 10 2016 209 769.5 filed Jun. 3, 2016 and DE 10 2016 213 422.1 filed Jul. 22, 2016, the entire disclosures of which are hereby incorporated by reference.

BACKGROUND OF THE INVENTION

The invention concerns a modular blood warmer. The invention also concerns a method for manufacturing and for operating a blood warmer of this type.

DE 11 2012 002 052 T5 discloses a fluid heating device comprising a fluid channel, a heat transfer element, a fluid channel transition point and a heating element which is disposed next to the heat transfer element. The blood can be heated to a desired temperature and be maintained at this temperature by means of a control device.

Hygiene or protection against soiling disadvantageously requires additional measures such as materials that prevent growth or fouling as specified in the mentioned application. Disadvantageously, the temperature of the fluid tracks the temperature which is preset by the control device only with a time delay. This can cause overshoots in the adjustment of the temperature.

WO 2004/098675 A2 discloses a line for transporting fluids, in particular body fluids. The line may be insulated. A thermal sensor and heating elements as well as a thermal medium may be arranged on the transport line.

Further blood warmers are disclosed in US 2009/0012655 A1, DE 27 50 418 A1 and US 2010/0327492 A1 and DE 10 2014 013 419 A1. Fluid warmers are also disclosed in WO 2014/118487 A1 and EP 0247989 B1.

These also disadvantageously require additional hygienic measures to be taken as protection against soiling or the disclosed blood warmers have an only insufficient coupling to the heating element.

For this reason, it is the underlying purpose of the present invention to provide a blood warmer in which soiling of the heat transfer surface can be prevented in a simple fashion and also in which the time delay, with which the temperature of the blood in the blood warmer tracks the temperature preset by the control device, is as small as possible. It is furthermore the object of the present invention to provide a method for operating and for manufacturing a blood warmer of this type.

SUMMARY OF THE INVENTION

This object is achieved by a blood warmer in accordance with the independent claim. The features of the inventive method are specified in the principal method claim. Advantageous embodiments can be extracted from the respective dependent claims.

The blood warmer in accordance with the invention comprises an inlet and an outlet for blood as well as a first and a second heating plate and an exchangeable conductor for the blood. The conductor has an indirect or direct fluidic connection to the inlet and the outlet. The conductor is arranged between the first heating plate and the second heating plate. The blood warmer is characterized in that a medium, which has a higher thermal conductivity than air, is arranged at least partially statically in an intermediate space, which remains between the first and/or the second heating plate and the conductor.

If the conductor or the heating plate has a rough surface, one or more intermediate spaces are generated between the conductor and the respective heating plate. These intermediate spaces are in fact small but impede good heat transfer. The medium located in the intermediate space or spaces then advantageously ensures good thermal coupling between the conductor and the heating plates. For this reason, even when the surfaces of the conductor or heating plate are rough, the temperature of the blood may be quickly adjusted to the preset temperature of the heating plates without e.g. the occurrence of temperature overshoots.

In this case, a less expensive conductor having a simple construction can be used for blood warming, which is removed after warming the blood and is replaced by a new conductor. This means an exchangeable conductor can be used. The term exchangeable conductor in this case means, in particular, a conductor which can be removed from and also be inserted into the blood warmer in a reversible fashion without destruction and/or without the use of tools. This advantageously does not require any expensive measures to be taken for cleaning the conductor or the heating plate. The blood warmer can in general also be used as a fluid warmer.

The medium may be present in the form of a fluid.

In one advantageous embodiment, the medium comprises water. The cost of warming blood can advantageously be kept comparatively low by using water as the medium. The thermal conductivity of air at room temperature typically assumes values of 0.025 W/(m·K), whereas that of water assumes values of 0.556 W/(m·K). The medium may comprise mixtures, in particular, a mixture of water and a disinfectant.

In one advantageous embodiment, the medium comprises a cleaning agent and/or a disinfectant by means of which in particular soiling can be removed from the blood warmer by wiping. Cleaning agents and/or disinfectants advantageously offer further protection against soiling. After use, an agent of this type is still in liquid form and for this reason, the surface of the heating plates can be cleaned in a simple fashion, i.e. soiling that could deteriorate the heat transfer is dissolved in the liquid and can be simply wiped away after use of the blood warmer when the conductor is removed.

The disinfectant may e.g. be a type of alcohol which has a boiling temperature of approximately 60° C. or above, i.e. is destroyed above the desired temperature range of the blood which is destroyed at a temperature of approximately 46° C. and above. The medium advantageously has a boiling point of between 60° C. and 300° C., in particular between 80° C. and 200° C. The thermal conductivity of the medium is advantageously between 0.1 W/(m·K) and 10 W/(m·K), in particular between 0.2 W/(m·K) and 0.6 W/(m·K). The thermal conductivity of e.g. ethanol as medium at room temperature is typically 0.185 W/(m·K).

Another embodiment of the blood warmer is characterized in that the conductor has a circular edge in cross-section and the edge of the first and/or the second heating plate and/or the edge of at least one recess in at least one of these heating plates has the shape of a sector of a circle in cross-section. In this fashion, the blood is heated in the conductor in a particularly uniform fashion.

One advantageous embodiment of the blood warmer is characterized in that the blood warmer comprises at least one access through which the medium can be introduced into the intermediate space, in particular, an access for a pump and/or a manual pump bellows and/or a syringe. The access may be designed in the form of a through-hole in a heating plate. In this fashion, the medium may advantageously be introduced in a simple fashion into the intermediate space or the intermediate spaces between the heating plates and the conductor. Since the intermediate spaces are small, the volume of the required medium is also small, in particular smaller than 2 ml.

One advantageous embodiment of the blood warmer is characterized in that a bag is arranged between the heating plates, in particular next to the intermediate space, which accommodates the medium such that the medium can be pressed out of the bag and can enter into the intermediate space when the two heating plates are brought together. The medium may advantageously be stored in the bag for a long period of time and be introduced, when required, into the at least one intermediate space without additional accessories.

One advantageous embodiment of the blood warmer is characterized in that the blood warmer comprises an arbor which can be pressed into the bag and/or can pierce the bag when the first and the second heating plates are moved towards one another. In an advantageous fashion, the medium can be introduced in a particularly effective fashion into the at least one intermediate space by opening the bag with the arbor.

The medium may be contained in a sponge, wherein at least part of the medium enters into the at least one intermediate space when the heating plates are brought together. A sponge in accordance with the invention means any material that is able to absorb a fluid and to at least partially release this fluid again when squeezed by a user.

A further embodiment of the blood warmer is characterized in that a sponge is arranged in the bag.

A further embodiment of the blood warmer is characterized in that the conductor comprises stainless steel, in particular X5CrNi18-10 (V2A). In this case, a biocompatible coating of the conductor can be omitted.

A further embodiment of the blood warmer is characterized in that the conductor is rigid. When the conductor is rigid, the blood warmer can also be operated in the vacuum range, e.g. in case of rinsing or dialysis or if the blood warmer is arranged well above the patient.

A further embodiment of the blood warmer is characterized in that the conductor is flexible.

One advantageous embodiment of the blood warmer is characterized in that the blood warmer comprises an electromechanical oscillating circuit and/or a vibration motor. Air bubbles collect at the boundary layer between the blood and the conductor and adhere in particular to the conductor. They grow until they reach a volume at which they are washed away. The air bubbles may advantageously be excited and put into motion by the vibrations caused at least temporarily by an electromechanical oscillating circuit or a vibration motor in such a fashion that they are already washed away prior to reaching that volume. The vibrations may moreover improve intermixing of the fluid to improve thermal distribution. The use of a vibration motor improves heat transfer, obtains a more uniform or more homogeneous outlet temperature of the blood and prevents standstill zones in the edge area and therefore reduces the danger of a haemolysis. The vibration motor may, in particular, be arranged on the heating plates. In particular, an electromotor with an imbalance, i.e. an eccentric, can be used as vibration motor. The vibration motor is preferably designed to achieve rotational speeds of more than 1000 rpm, in particular, of more than 5000 rpm. A blood warmer in accordance with the claims and the associated description with a vibration motor is regarded as a separate invention, in particular irrespective of a medium.

One advantageous embodiment of the blood warmer is characterized in that the blood warmer is provided with at least one possibility of coupling a temperature sensor. The coupling possibility may be designed in the form of a through-hole in a heating plate. Advantageously, the temperature of the blood in the blood warmer can be controlled by coupling a temperature sensor.

A further embodiment of the blood warmer is characterized in that, between the heating plates, a first conductor is fluidically arranged directly behind the inlet and a second conductor is fluidically arranged directly in front of the outlet, wherein the first and the second conductor are indirectly or directly fluidically connected and no further conductors are spatially arranged between the first and the second conductor.

One advantageous embodiment of the blood warmer is characterized in that, between the heating plates, a plurality of conductors are arranged in addition to the first and the second conductor, wherein all conductors are preferably arranged parallel to one another, and the conductors are fluidically connected and arranged in such a fashion that the direction in which the blood can flow in one conductor is opposite to the direction in which the blood can flow in the respective conductor fluidically disposed downstream. This "labyrinth-like" arrangement of the conductors advantageously enables the blood to be kept and uniformly warmed in the blood warmer for a particularly long time.

One advantageous embodiment of the blood warmer is characterized in that for each temperature sensor two coupling possibilities are provided between the first and the second conductor. In this way, the temperature of the blood can advantageously be controlled at the coldest point, i.e. at the inlet, and also at the warmest point, i.e. at the outlet.

One advantageous embodiment of the blood warmer is characterized in that the fluidic connections between the conductors are rigid and comprise, in particular, plastic material or metal and/or are bent from one part. The fluidic connections can then advantageously be arranged on the conductors in a particularly simple fashion. The fluidic connections may, in particular, be channels in a component produced by injection molding. By arranging the component or a plurality of such components on the heating plates, all fluid connections can simultaneously be arranged on the conductors.

A further embodiment of the blood warmer is characterized in that the wall of the conductor has depressions which extend like a groove or spiral along the wall of the conductor and/or an insert is arranged in the conductor which can generate swirling in the flow profile of the blood. The spatial differences between the depressions and the elevated areas formed between the depressions are thereby sufficiently small such that the heat flow across the conductor wall is homogeneous due to the arrangement of the medium in the intermediate spaces between the heating plates and the respective conductor. In an advantageous fashion, swirling in the flow profile of the blood generated by a profile with depressions or grooves similar to a thread or by a suitable insert in the conductor improves intermixing of the blood. The insert may, in particular, comprise a helical profile.

In one method for operating an inventive blood warmer, a conductor which is suitable for the passage of blood is arranged between the first heating plate and the second heating plate and is fluidically connected to an inlet and an outlet for blood. A medium, which has a higher thermal conductivity than air, is at least partially statically arranged in at least one intermediate space which remains between the first and/or the second heating plate and the conductor.

When a plurality of temperature sensors are used, it is possible to determine which temperature sensor shows the maximum blood temperature during warming of the blood. For controlling the heating plates, it can then be determined that the temperature at this temperature sensor must never exceed a predetermined temperature value, in particular 46° C.

One advantageous method for operating the blood warmer is characterized in that the heating plates are switched off at a time interval after start of heating of the heating plates and are switched on again after a certain time interval, wherein switching off and subsequent switching on of the heating plates is preferably repeated several times. The temporal development of the temperature change of the blood as a reaction to the temperature change of the heating plates is determined in each case at least between switching off and subsequent switching on of the heating plates. The temporal dependence of the values of the parameters which determine the heating power of the heating plates is determined from these temperature changes of the heating plates and the respective temperature changes of the blood in such a fashion that, firstly, the blood reaches the desired temperature value within a minimum time and after reaching the desired temperature value the temperature does not exceed a predetermined temperature value, which is not harmful to the blood and which is above or equal to the desired temperature value and, secondly, a point in time exists starting from which the temperature of the blood is kept at a constant level at the desired temperature value.

In particular, the heating plates may be switched off for a time interval which is considerably shorter than the time lapsed after start of heating of the heating plates. The time interval may be in the range of some seconds, in particular 5 seconds. The time lapsed after start of heating of the heating plates may be in the range of some minutes, in particular four minutes. Switching off and switching on of the heating plates advantageously permits statements about the temperature distribution of the blood warmer and the heat flow between the heating plates and the blood, in particular, with respect to the size and homogeneity of the heat flow as well as with respect to the power transfer by the blood warmer. In this fashion, temperature control adjustment is improved for optimum heat transfer to obtain the desired blood temperature.

Further features and advantages of the invention can be extracted from the following detailed description of an embodiment of the invention, from the claims and the figures of the drawing which shows details which are essential to the invention. The various features may be used individually or collectively in various combinations in variants of the invention. The features shown in the drawing are illustrated in such a way that the inventive distinctive features are made clearly visible.

DESCRIPTION OF THE PREFERRED EMBODIMENT

Figure 1:
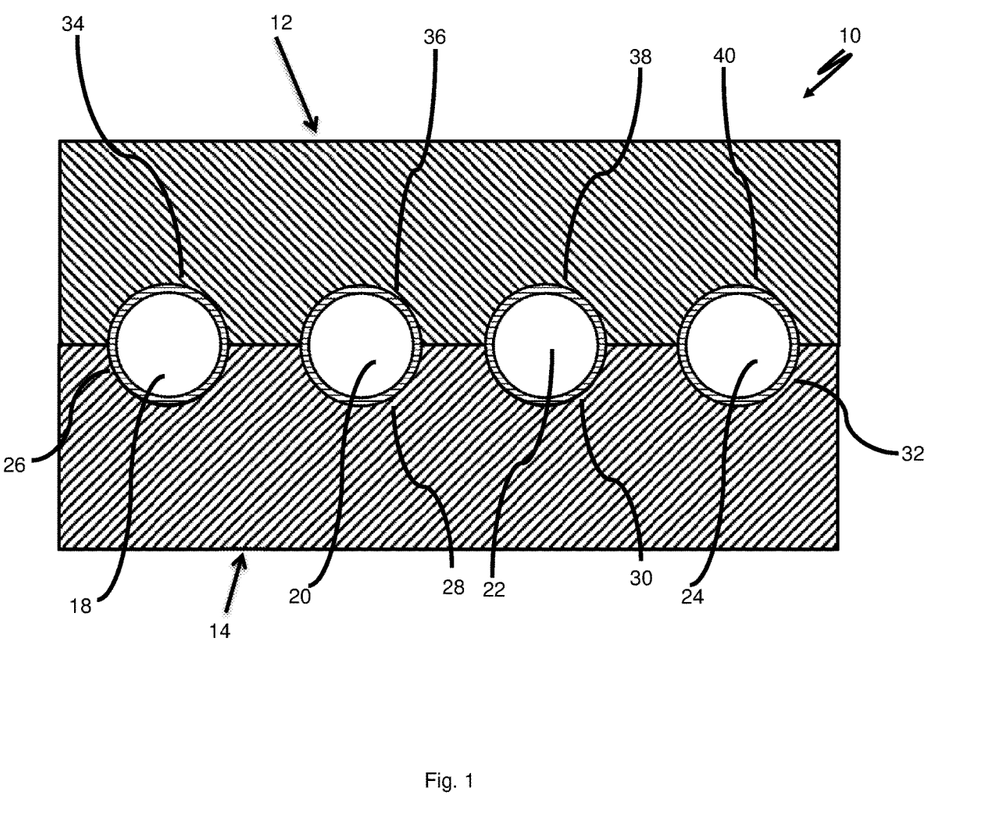
FIG. 1 shows a cross-section through the inventive blood warmer.

FIG. 1 shows a cross-section through an inventive blood warmer 10. It comprises a first heating plate 12 and a second heating plate 14. Four conductors, which are suited for transporting blood, have the form of conducting tubes 18, 20, 22, 24 with circular cross-section and are arranged at a separation from one another between the heating plates 12, 14. The heating plates 12, 14 have circular recesses 26, 28, 30, 32 or 34, 36, 38, 40 in which the conducting tubes 18, 20, 22, 24 are arranged in a substantially form-locking fashion.

Figure 2:
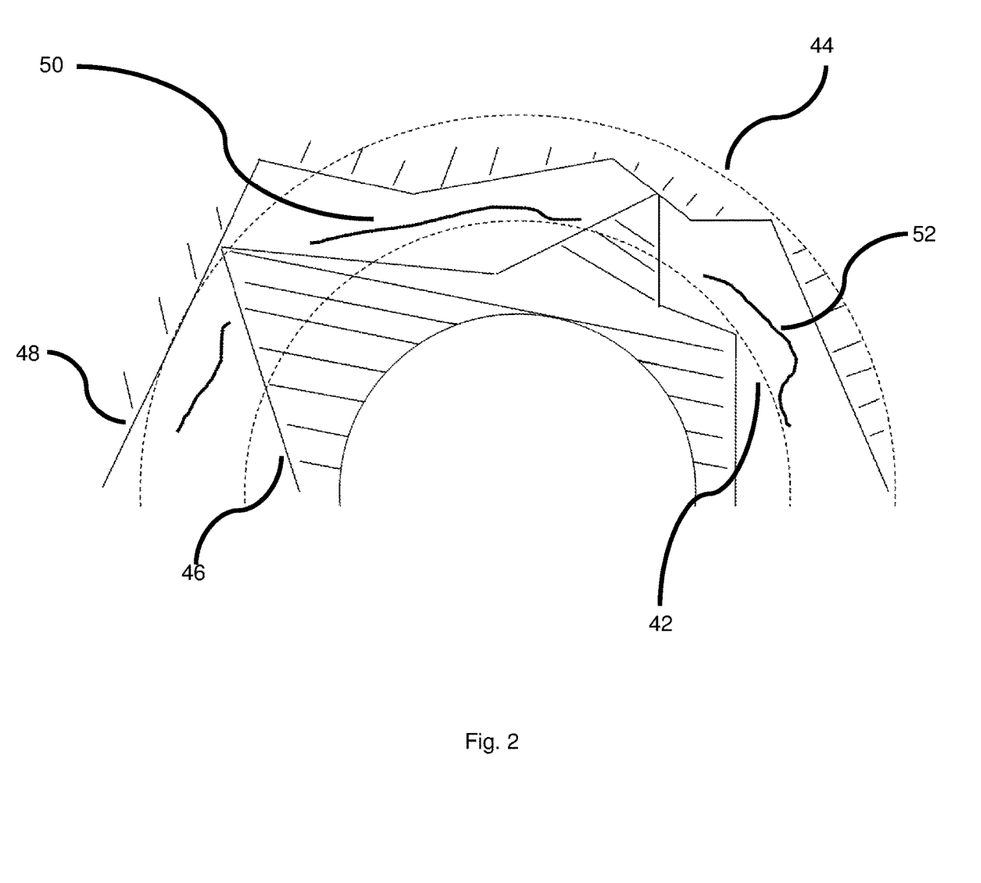
FIG. 2 shows a cross-section of the area of the edges between one of the conductors and the respective recess.

FIG. 2 shows the cross-section of the area of the edges between one of the conducting tubes 18, 20, 22, 24 and the respective recess 26, 28, 30, 32 or 34, 36, 38, 40 of one of the heating plates 12, 14. The ideal circular shape 42 of the surface of the conducting tube 18, 20, 22, 24 is shown in dashed lines in profile and the ideal circular shape 44 of the surface of the recess 26, 28, 30, 32, or 34, 36, 38, 40 is shown in profile. These ideal shapes 42, 44 are disposed on top of each other in the inventive blood warmer but are shown at a separation from one another in this schematic view for reasons of clarity. The solid lines schematically show the actual rough shape of the surface 46 of the respective conducting tube 18, 20, 22, 24 in profile and the actual rough shape of the surface 48 of the respective recess 26, 28, 30, 32 or 34, 36, 38, 40 in profile. At least one intermediate space 50 is generated by the roughness of the surface of the respective heating plate 12, 14 and the respective conducting tube 18, 20, 22, 24. This intermediate space 50 causes deterioration of the heat exchange between the respective heating plate 12, 14 and the respective conducting tube 18, 20, 22, 24. By filling the at least one intermediate space 50 with a medium 52, which has a higher thermal conductivity than air, the heat flow from the respective heating plate 12, 14 to the respective conducting tube 18, 20, 22, 24 can be improved. The medium 52 is schematically illustrated by curved lines.

Figure 3A:
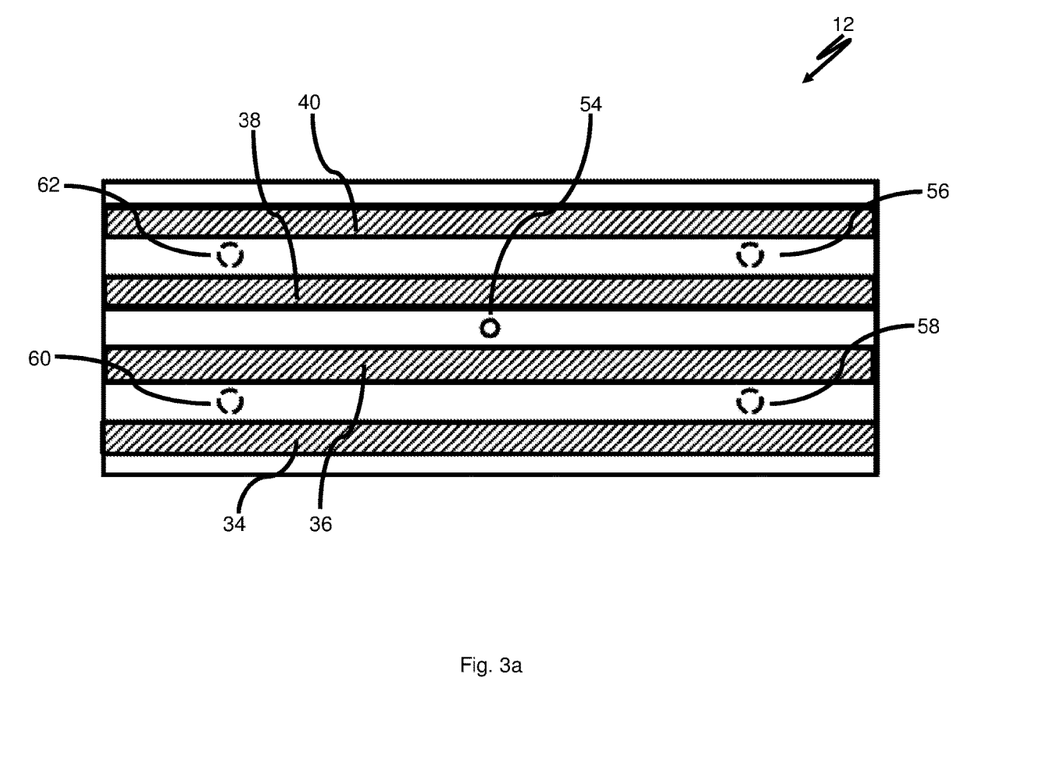
FIG. 3a shows a top view of a heating plate of the blood warmer according to the invention.

By way of example, FIG. 3a shows a top view of one of the two heating plates 12, 14 of the inventive blood warmer 10, in this case the heating plate 12. The blood warmer 10 has an access 54 in the form of an opening through which the medium 52 (see FIG. 2) can be introduced into the at least one intermediate space 50 (see FIG. 2) between the heating plates 12, 14 and the conducting tubes 18, 20, 22, 24. The recesses 34, 36, 38, 40 are shown with hatched lines. Contacts 56, 58, 60, 62 for temperature sensors are arranged between the recesses 34, 36, 38, 40. Two of the contacts 56, 58, 60, 62 for temperature sensors are arranged between two of the recesses 34, 36, 38, 40 for the conducting tubes 18, 20, 22, 24 in each case. The contacts 56, 58, 60, 62 for the temperature sensors are arranged symmetrically with respect to the symmetry axes of the heating plate 14 in the top view.

Figure 3B:
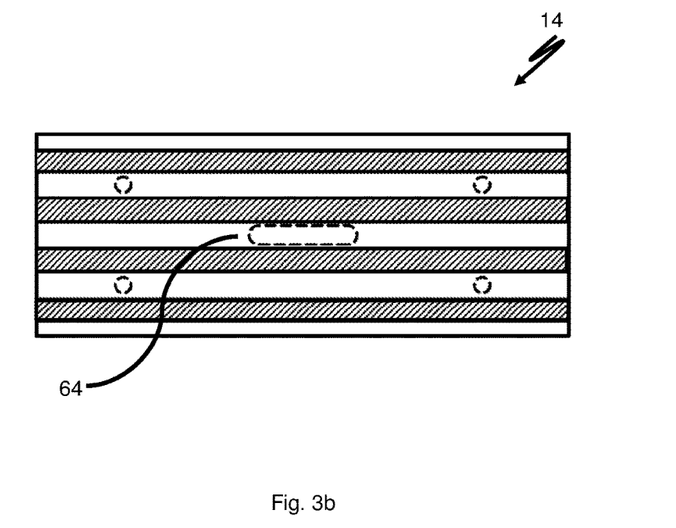
FIG. 3b shows a top view of a heating plate with a bag for the medium.

FIG. 3b shows a top view of the heating plate 14 of FIG. 1a with a bag 64 or a sponge for the medium, in particular a fluid, with which the medium can be introduced into the blood warmer 10.

Figure 4:
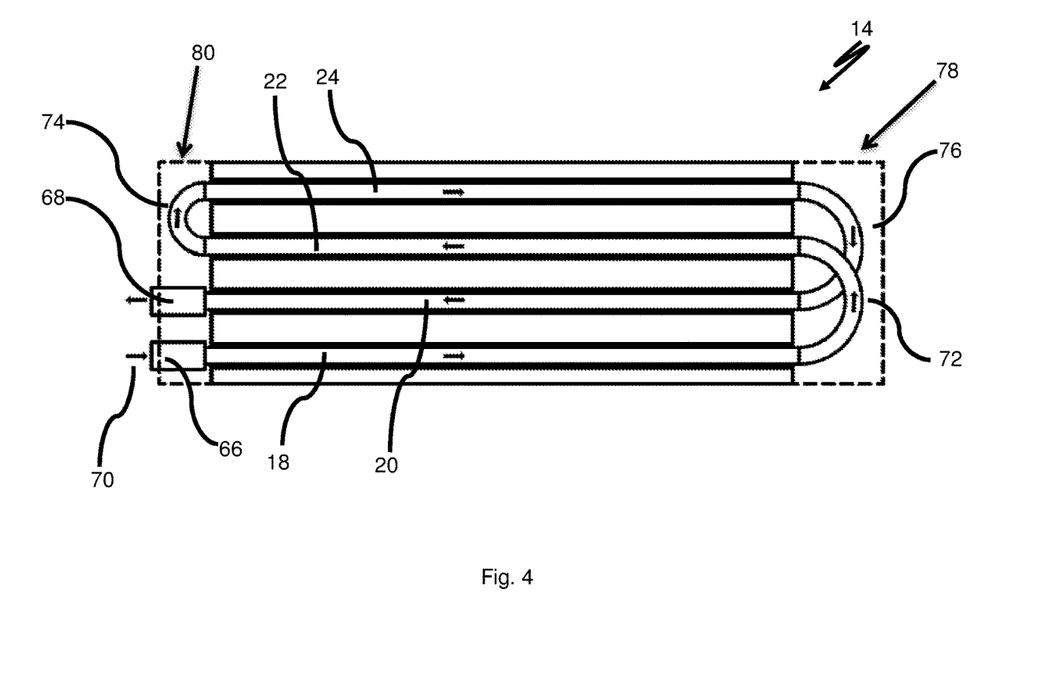
FIG. 4 shows a top view of one of the heating plates of the inventive blood warmer with a plurality of conductors.

FIG. 4 shows a top view of the heating plate 14 of the inventive blood warmer 10 with the conducting tubes 18, 20, 22, 24. An inlet 66 is arranged on the conducting tube 18. An outlet 68 is arranged on the conducting tube 20. There is no further conducting tube 18, 20, 22, 24 spatially arranged between the conducting tube 18 and the conducting tube 20. The flow 70 of the blood is illustrated by thick black arrows. Fluidic connections 72, 74, 76 are arranged between the conducting tubes 18, 20, 22, 24. These may be designed to be flexible, in particular in the form of hoses. As an alternative, they may also consist of a rigid material. They may, in particular, also be arranged or formed in rigid components 78, 80 which were produced e.g. by injection molding. In this fashion, the fluidic connections 72, 74, 76 can be simply and simultaneously arranged on the conducting tubes 18, 20, 22, 24. At least one fluidic connection 72, 74, 76, in particular a plurality of fluidic connections 72, 74, 76, preferably all fluid connections 72, 74, 76 may be designed in the form of (one) curved line(s).

Figure 5:
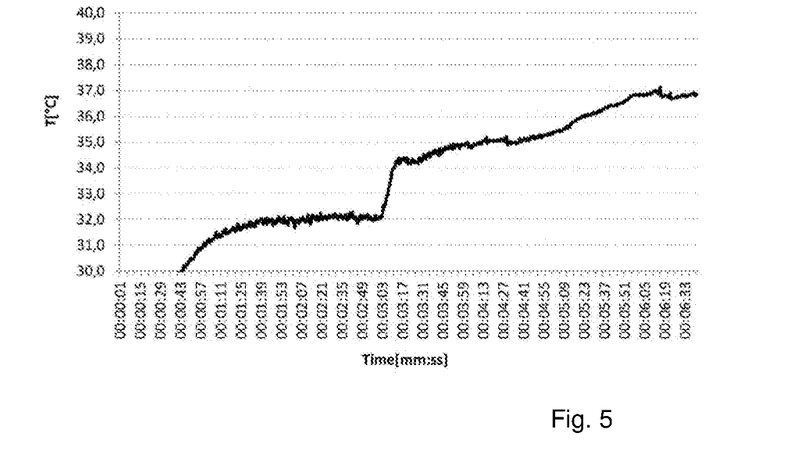
FIG. 5 shows a temporal dependence of warming the blood by the blood warmer.

FIG. 5 shows the temporal dependance of warming the blood at the exit of the blood warmer. The time axis shows the time in minutes, the temperature axis shows the temperature of the blood in degree Celsius. The initial temperature of the blood at zero minutes and zero seconds is between 10° C. and 20° C. At the start, there is no medium 52 (see FIG. 2) arranged in the respective intermediate spaces 50 (see FIG. 2) between the edges of the conducting tubes 18, 20, 22, 24 (see FIG. 1) and the edges of the recesses 26, 28, 30, 32 or 34, 36, 38, 40. After 3 minutes a medium 52 in the form of a fluid, here in particular in the form of water, is distributed in the respective intermediate spaces 50 through an opening (see access 54 in FIG. 3a). It is clearly shown that until then the temperature of blood rises comparatively slowly. Starting from that time when the medium is added, the temperature jumps from approximately 32° C. to approximately 34° C. within a time interval of approximately 10 seconds. Thereafter, the temperature also increases more quickly than prior to addition of the medium. After another approximately 3 minutes, the blood assumes temperature values below the temperature of the heating plates 12, 14.

Figure 6:
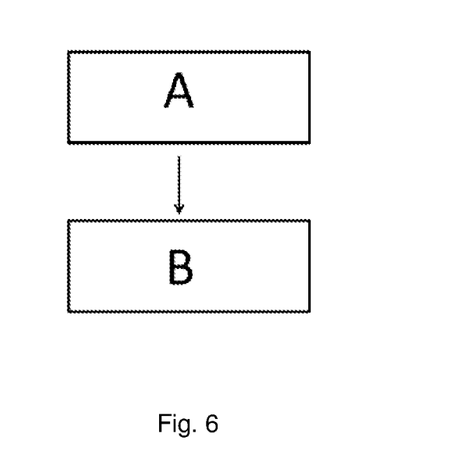
FIG. 6 shows a method for manufacturing or operating the blood warmer.

FIG. 6 shows a method for manufacturing or operating a blood warmer 10 as described above. In a method step A, a conductor 18 which is suited for the passage of blood and can be exchanged is arranged between the first heating plate 12 and the second heating plate 14 and is fluidically connected to an inlet 66 and an outlet 68 for blood. In a method step B, a medium 52, which has a higher thermal conductivity than air, is at least partially statically arranged in at least one intermediate space 50 which remains between the first heating plate 12 and/or the second heating plate 14 and the conductor 18.

Figure 7:
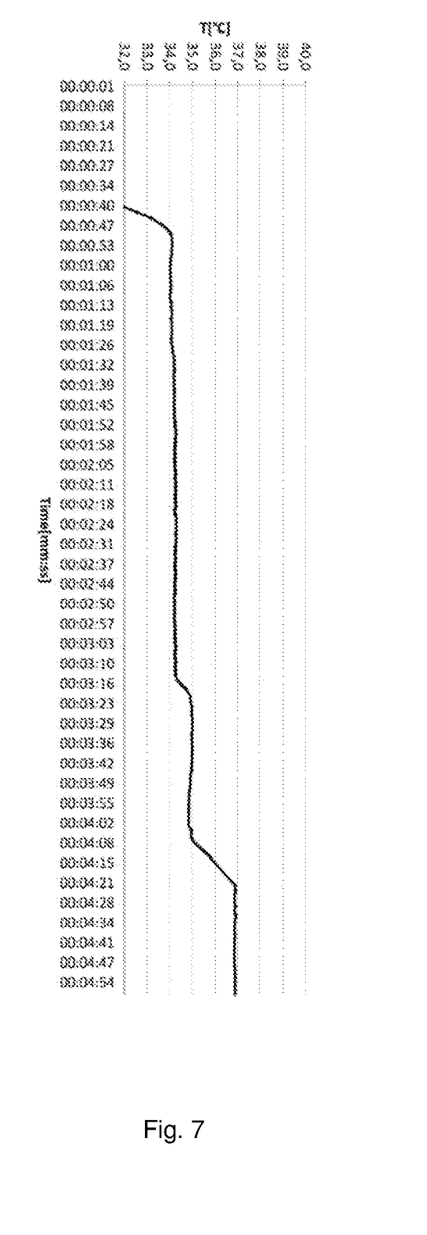
FIG. 7 shows a temporal dependence of warming the blood with the use of a vibration motor.

FIG. 7 shows the temporal dependence of warming the blood with the use of a vibration motor and upon exiting the blood warmer. The time axis shows the time in minutes, the temperature axis shows the temperature of the blood in degrees Celsius. The temperature of the blood at the inlet is less than 20° C. The initial temperature of the blood at the outlet at zero minutes and zero seconds is 20° C. The flow 70 of the blood (see FIG. 4) through the cross-section of the outlet is 200 ml/min. At the start, there is no medium 52 (see FIG. 2) arranged in the respective intermediate spaces 50 (see FIG. 2) between the edges of the conducting tubes 18, 20, 22, 24 (see FIG. 1) and the edges of the recesses 26, 28, 30, 32 or 34, 36, 38, 40. The vibration motor is continuously switched on from the beginning at a voltage of 1.5 V and starting from the point in time of zero minutes and zero seconds. After approximately 3 minutes and 15 seconds a medium 52 in the form of water is distributed in the respective intermediate spaces 50 between the edges of the recesses 30, 32, or 38, 40 and the edges of the conducting tubes 22, 24, which are not fluidically connected to the outlet or the inlet. This significantly increases the temperature of the blood within approximately 8 seconds from approximately 34.2° C. to approximately 35° C. After approximately 4 minutes, medium 52 in the form of water is distributed in the respective intermediate spaces 50 between the edges of the recesses 26, 28 or 34, 36 and the edges of the conducting tubes 18, 20 which are each fluidically connected to the outlet or the inlet. This further sharply increases the temperature from approximately 35° C. to approximately 37° C. within a time period of approximately 13 seconds. It then remains at a constant level. In comparison with the temperature curve in FIG. 5, the temperature curve in FIG. 7 shows clearly smaller fluctuation amplitudes or almost no upper or lower fluctuation amplitudes. The vibrations of the continuously switched-on vibration motor thus cause a substantially more uniform temperature distribution in the blood than without a vibration motor.

Figure 8:
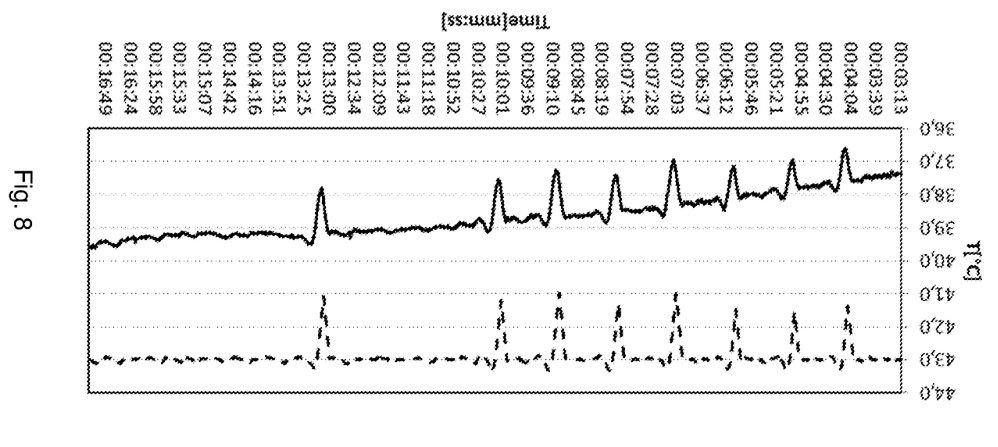
FIG. 8 shows a temporal dependence of warming the blood when the heating plates are switched off and switched on again several times.

FIG. 8 shows the temporal development of warming of the blood upon exiting the blood warmer with the use of a vibration motor when the heating plates 12, 14 are switched off several times and are switched on again after a certain time interval. The time axis shows the time in minutes, the temperature axis shows the temperature of the blood as well as the temperature of the heating plates 12, 14 in degrees Celsius. The temperature of the blood at the inlet is 20° C. The temperature of the blood at the outlet is illustrated by solid lines. The temperature of the heating plates 12, 14 is illustrated by dashed lines. The temperature of the blood at the start of measurement after previous warming over a time period of approximately 3 minutes and 13 seconds is at approximately 37.4° C. The flow 70 of the blood through the cross-section of the outlet is approximately 200 ml/min. Water is arranged as medium 52 (see FIG. 2) in the respective intermediate spaces 50 (see FIG. 2) between the edges of the conducting tubes 18, 20, 22, 24 (see FIG. 1) and the edges of the recesses 26, 28, 30, 32 or 34, 36, 38, 40. The vibration motor is continuously operated at a voltage of e.g. 1.5 V during the overall measurement. The heating plates 12, 14 are operated at a temperature of approximately 43° C. After approximately 4 minutes, the heating plates 12, 14 are switched off. Synchronously to the temperature reduction of the heating plates 12, 14 to approximately 41.3° C. a decrease of the temperature of the blood at the outlet to approximately 36.6° C. can be noticed. The heating plates 12, 14 are switched on again after approximately 5 seconds. Synchronously to the increase in temperature of the heating plates 12, 14, the temperature of the blood at the outlet also increases. This procedure is repeated several times in order to be able to make statements concerning the behavior of the heat flow.

Figure 9:
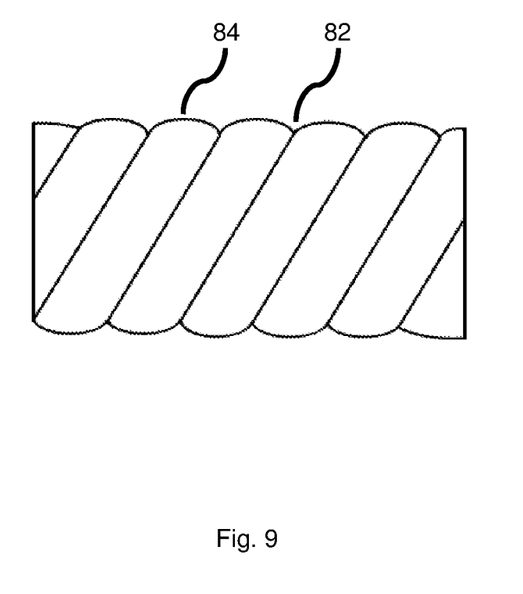
FIG. 9 shows a conductor with spiral depressions along the wall.

FIG. 9 schematically shows a side view of a section of a conducting tube 18, 20, 22, 24 with at least one depression 82 extending in a spiral fashion along the wall of the conducting tube 18, 20, 22, 24. Between this helical depression 82 with the shape of a thread, corresponding elevated sections 84 are formed which have a bent profile in cross-section.

Figure 10:
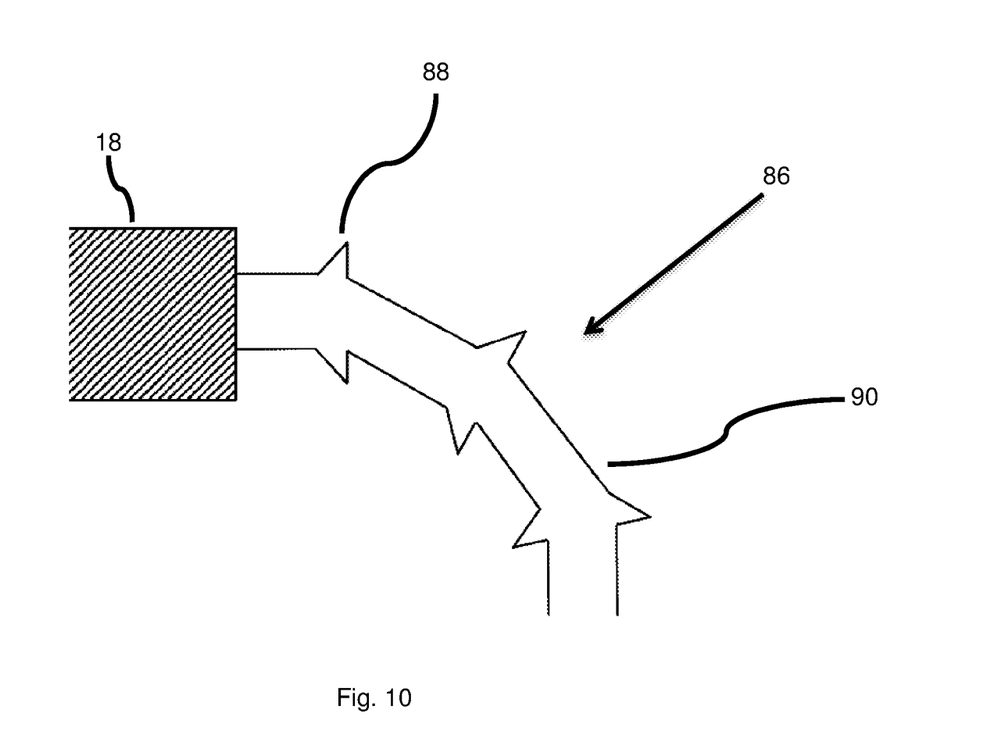
FIG. 10 shows a conductor with an insert.

FIG. 10 shows an insert 86 which can be arranged in a conducting tube 18, 20, 22, 24, here as an example the conducting tube 18. The insert 86 has protruding sections 88 between which connecting sections 90 are formed.

According to FIG. 4, the blood flows during operation through the inlet 66 into the conducting tube 18, subsequently through the fluidic connection 72 into the conducting tube 22 and then through the fluidic connection 74 into the conducting tube 24 and then through the fluidic connection 76 into the conducting tube 20. The blood flows from the conducting tube 20 to the outlet 68. In each of the conducting tubes 18, 20, 22, 24, the direction of flow 70 of the blood is opposite to the direction of flow 70 of the blood in the respective associated downstream conducting tube 18, 20, 22, 24. The temperature of the blood is regulated in each case by heating or cooling the heating plates 12, 14 when one of the temperature sensors, which are arranged at the contacts 56, 58, 60, 62 for the temperature sensors, shows a temperature which is above or below the desired range. The medium 52 which fills the respective intermediate spaces 50 between the conducting tubes 18, 20, 22, 24 and the heating plates 12, 14, thereby ensures rapid heat transfer between the heating plates 12, 14 and the conducting tubes 18, 20, 22, 24. In this fashion, the temperature of the blood can be maintained in the desired range without overshoots. During operation, the heating plate temperature is preferably regulated on the basis of the temperature sensor that measures the maximum temperature.

In summary and in a synopsis of all figures of the drawing, the invention thus concerns a modular blood warmer 10. The blood warmer 10 comprises a first heating plate 12 and a second heating plate 14. It moreover comprises an exchangeable conductor 18, 20, 22, 24 for blood, which is arranged between the first heating plate 12 and the second heating plate 14. The blood warmer 10 moreover has an inlet 66 and an outlet 68 for blood. The conductor 18, 20, 22, 24 is fluidically indirectly or directly connected to the inlet 66 and the outlet 68. Due to the roughness of the surface 46 of the conductor 18, 20, 22, 24, at least one intermediate space 50 remains between the first heating plate 12 and/or the second heating plate 14 and the conductor 18, 20, 22, 24. A medium 52, which has a higher thermal conductivity than air, is at least partially statically arranged in the intermediate space 50. The modular blood warmer 10 may alternatively or additionally comprise an electromechanical oscillating circuit and/or a vibration motor. The conductor 18, 20, 22, 24 may comprise at least one depression 82 which is formed like a spiral along the lateral area of the conductor 18, 20, 22, 24.

We claim:

1. A blood warmer comprising:
an inlet for blood;
an outlet for blood;
a first heating plate;
a second heating plate;
an exchangeable rigid conductor for the blood, wherein said rigid conductor is directly or indirectly fluidically connected to said inlet and said outlet, said rigid conductor being disposed between said first heating plate and said second heating plate;
a medium, said medium having a higher thermal conductivity than air and being at least partially statically disposed in an intermediate space which remains between said rigid conductor and said first heating plate and/or which remains between said rigid conductor and said second heating plate, wherein said intermediate space is defined by a surface roughness of said first heating plate, of said second heating plate and/or of said rigid conductor; and
a bag disposed between said first and said second heating plates and next to said intermediate space, wherein said medium is disposed in said bag such that said medium is pressed out of said bag and enters said intermediate space when said first and said second heating plates are brought together.

2. The blood warmer of claim 1, wherein said medium comprises water.

3. The blood warmer of claim 1, wherein said medium has a cleaning agent, a disinfectant and/or an agent facilitating removal of soiling from the blood warmer by wiping.

4. The blood warmer of claim 1, wherein said rigid conductor has a circular edge in cross-section and said first heating plate, said second heating plate, an edge of at least one recess in said first heating plate along said rigid conductor, and/or an edge of at least one recess in said second heating plate along said rigid conductor, has a shape of a sector of a circle in cross-section.

5. The blood warmer of claim 1, wherein the blood warmer has at least one access through which said medium is introduced into said intermediate space.

6. The blood warmer of claim 5, wherein said access is adapted to accommodate a pump, a manual pump bellows and/or a syringe.

7. The blood warmer of claim 1, wherein the blood warmer further comprises an arbor which is pressed into said bag and/or which pierces said bag when said first heating plate and said second heating plate are moved towards one another.

8. The blood warmer of claim 1, wherein the blood warmer further comprises an electromechanical oscillating circuit and/or a vibration motor.

9. The blood warmer of claim 1, wherein the blood warmer has at least one coupling possibility for a temperature sensor.

10. The blood warmer of claim 1, wherein said rigid conductor comprises a first rigid conductor which is fluidically directly disposed between said first and said second heating plates downstream of said inlet and a second rigid conductor which is fluidically directly disposed between said first and said second heating plates upstream of said outlet, wherein said first conductor and said second rigid conductor are fluidically indirectly or directly connected and no further conductors are spatially disposed between said first rigid conductor and said second rigid conductor.

11. The blood warmer of claim 9, wherein said rigid conductor comprises a first rigid conductor which is fluidically directly disposed between said first and said second heating plates downstream of said inlet and a second rigid conductor which is fluidically directly disposed between said first and said second heating plates upstream of said outlet, wherein said first rigid conductor and said second rigid conductor are fluidically indirectly or directly connected and no further conductors are spatially disposed between said first rigid conductor and said second rigid conductor.

12. The blood warmer of claim 10, further comprising at least one additional rigid conductor disposed between said first and said second heating plates, wherein said first rigid conductor, said second rigid conductor and said additional rigid conductor are disposed in parallel and are fluidically connected and disposed in such a fashion that a direction in which the blood flows in one of said first rigid conductor, said second rigid conductor and said additional rigid conductor is opposite to a direction in which the blood flows in a respective directly adjacent fluidically downstream one of said first rigid conductor, said second rigid conductor and said additional rigid conductor.

13. The blood warmer of claim 11, wherein each of two temperature sensors has one said coupling possibility disposed between said first rigid conductor and said second rigid conductor.

14. The blood warmer of claim 10, wherein fluidic connections between said first and said second rigid conductors comprise a plastic material, comprise metal and/or are bent from one part.

15. The blood warmer of claim 1, wherein a wall of said rigid conductor has depressions which extend like a groove or spiral along said wall of said rigid conductor.

16. The blood warmer of claim 1, further comprising an insert disposed in said rigid conductor, wherein said insert is adapted to generate swirling in a flow profile of the blood or has a helical profile.

17. A method for operating a blood warmer, the blood warmer comprising:
   an inlet for blood;
   an outlet for blood;
   a first heating plate;
   a second heating plate;
   an exchangeable rigid conductor for the blood, wherein said rigid conductor is directly or indirectly fluidically connected to said inlet and said outlet, said rigid conductor being disposed between said first heating plate and said second heating plate; and
   a medium, said medium having a higher thermal conductivity than air and being at least partially statically disposed in an intermediate space which remains between said rigid conductor and said first heating plate and/or which remains between said rigid conductor and said second heating plate, said intermediate space being defined by a surface roughness of said first heating plate, of said second heating plate and/or of said rigid conductor,
wherein the method comprises the step of directing blood to flow through the rigid conductor, thereby heating the blood to a desired temperature, the method further comprising the steps of:
   a) heating the first heating plate and/or the second heating plate;
   b) switching off the first heating plate and/or the second heating plate at a first-time interval elapsed following a beginning of step a):
   c) switching on the first heating plate and/or the second heating plate at a second-time interval elapsed following a beginning of step b);
   d) determining, at least between steps b) and c), a temporal dependence of a temperature change of the blood as a reaction to a temperature change of the first heating plate and/or of the second heating plate; and
   e) determining a temporal dependence of values of parameters, which determine a heating power of the first heating plate and/or the second heating plate from results of step d) and respective temperature changes of the blood in such a fashion that the blood reaches a desired temperature value in a minimum amount of time, wherein the desired temperature value does not exceed a predetermined temperature value which is not dangerous for the blood after the desired temperature value has been reached and which is above or equal to the desired temperature value and such that there is a point in time starting from which the temperature of the blood is maintained at a constant level at the desired temperature value.

18. The method of claim 17, wherein steps b) and c) are repeated several times.

* * * * *